US009615736B2

(12) United States Patent
Yamashita

(10) Patent No.: US 9,615,736 B2
(45) Date of Patent: Apr. 11, 2017

(54) OPTICAL INTERFERENCE TOMOGRAPHIC APPARATUS, AND METHOD FOR CONTROLLING OPTICAL INTERFERENCE TOMOGRAPHIC APPARATUS

(71) Applicant: CANON KABUSHIKI KAISHA, Tokyo (JP)

(72) Inventor: Risa Yamashita, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 27 days.

(21) Appl. No.: 14/718,312

(22) Filed: May 21, 2015

(65) Prior Publication Data
US 2015/0342456 A1 Dec. 3, 2015

(30) Foreign Application Priority Data

May 30, 2014 (JP) ................. 2014-112609

(51) Int. Cl.
*A61B 3/14* (2006.01)
*A61B 3/10* (2006.01)
*G01B 9/02* (2006.01)

(52) U.S. Cl.
CPC .......... *A61B 3/102* (2013.01); *G01B 9/02044* (2013.01); *G01B 9/02075* (2013.01); *G01B 9/02083* (2013.01); *G01B 9/02091* (2013.01)

(58) Field of Classification Search
CPC .. A61B 3/102; A61B 3/14; A61B 3/12; A61B 3/0025; A61B 3/1225; A61B 3/0058; A61B 3/1025; A61B 5/0066; G06T 2207/10101; G06T 2207/30041; G06T 2207/10072; G06T 11/003; G01B 9/02091; G01B 9/0203

USPC .......................................................... 351/206
See application file for complete search history.

(56) References Cited

U.S. PATENT DOCUMENTS

| 9,084,562 B2 | 7/2015 | Kakuma |
| 2011/0228221 A1* | 9/2011 | Hanebuchi ............. A61B 3/102 351/206 |
| 2014/0192323 A1 | 7/2014 | Kakuma |

FOREIGN PATENT DOCUMENTS

| JP | 2011-214968 A | 10/2011 |
| JP | 2012-211797 A | 11/2012 |

* cited by examiner

*Primary Examiner* — Mahidere Sahle
(74) *Attorney, Agent, or Firm* — Fitzpatrick, Cella, Harper & Scinto

(57) ABSTRACT

In order to acquire a tomographic image of the eye to be inspected with high precision even in case where an optical path length and intensity vary depending on a scanned position in an OCT apparatus acquiring the tomographic image of a predetermined part of an object to be inspected, based on the intensity of interference light obtained by combining return light from the object that has been irradiated with the measuring light, with reference light corresponding to the measuring light, includes: a scanning optical system which scans the object with the measuring light in an optical path of the measuring light; an image forming unit which generates the tomographic image based on the intensity of the interference light; and an image correcting unit which subjects the tomographic image to a correction process appropriate to the scanned position with the measuring light on the object.

14 Claims, 4 Drawing Sheets

FIG. 3A
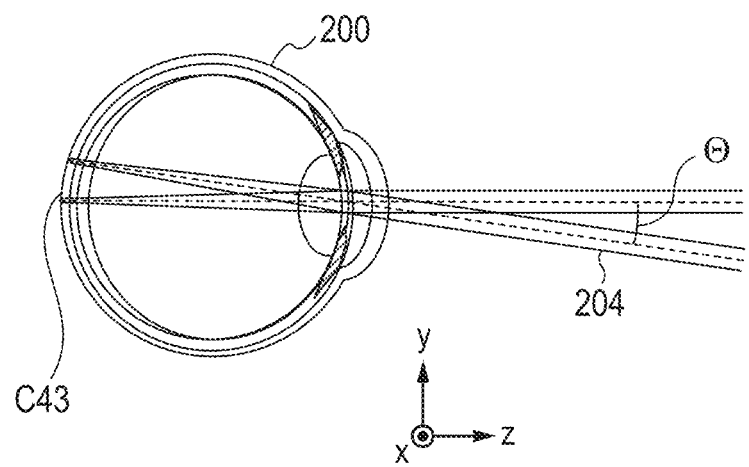
FIG. 3B
FIG. 3C
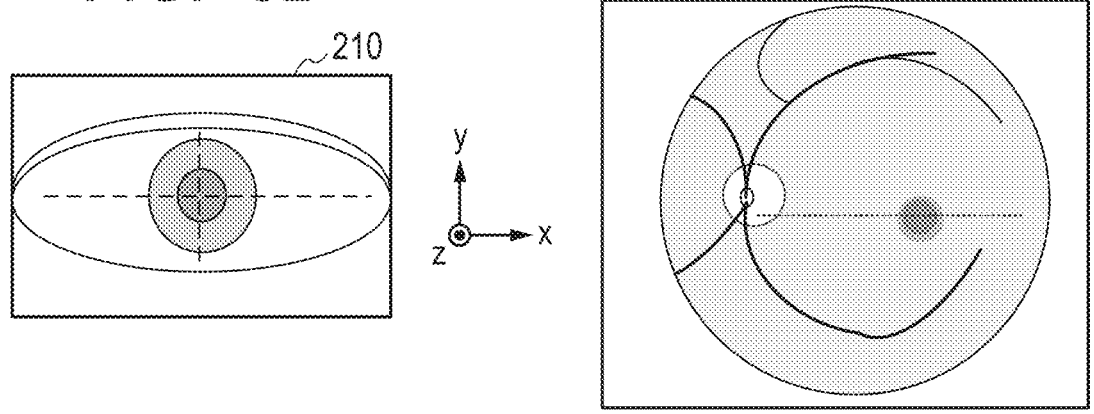
FIG. 4
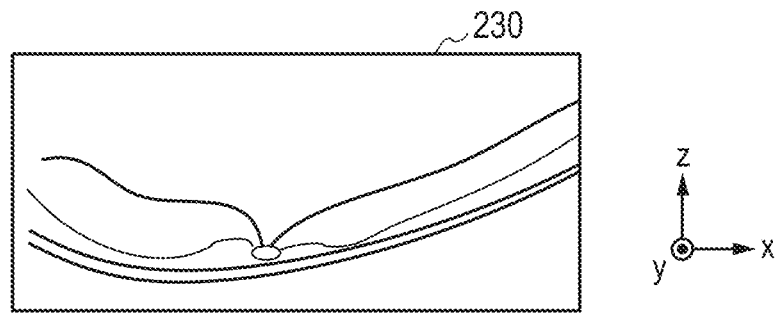

OPTICAL INTERFERENCE TOMOGRAPHIC APPARATUS, AND METHOD FOR CONTROLLING OPTICAL INTERFERENCE TOMOGRAPHIC APPARATUS

BACKGROUND OF THE INVENTION

Field of the Invention

The present invention relates to an optical interference tomographic apparatus, and a method for controlling the same.

Description of the Related Art

Currently, an optical interference tomographic apparatus (hereinafter referred to as OCT apparatus) for performing OCT (Optical Coherence Tomography) which uses interference of light waves is widely used in diagnosis in an ophthalmology field. This OCT apparatus divides light of a low-coherence light source into measuring light which irradiates an eye to be inspected, and reference light, and irradiates the eye to be inspected with the measuring light. After this, reflected light or back scattered light of the measuring light, which is obtained from the eye to be inspected, interferes with the reference light, and interference light is obtained. A tomographic signal at some position of the eye to be inspected can be acquired from the interference light. When the eye to be inspected is scanned with the measuring light, the tomographic signal inspected. A tomographic image can be composed by an operation of making each of the obtained tomographic signals correspond to measurement positions of the eye to be inspected, respectively.

Accordingly, such an OCT apparatus has generally a scanning mechanism of the measuring light in order to photograph a broad range of the eye to be inspected. A scanning mirror is widely adopted for these scanning mechanisms, which planarly scans the eye to be inspected through an optical component arranged in an optical path. Japanese Patent Application Laid-Open No. 2012-211797 shows an example in which a galvanometer mirror is adopted for the scanning mechanism.

The scanning mechanism with the use of the scanning mirror or the like scans the measuring light while changing the angle of the scanning mirror with respect to an optical component such as a lens and a dichroic mirror which are arranged in the optical path, in this case, the incident angle of a light beam on each of the optical components results in varying according to a scanning angle. When the incident angle of the light beam such as the measuring light varies, in the case of an optical component such as the dichroic mirror, which is used for reflection or transmission, reflection or transmission characteristics occasionally vary according to the incident angle of the light beam. In addition, in the case of the optical component such as the lens which is used in the transmission, when the incident angle of the light beam varies, an optical path length of the light beam results in varying according to the curvature and the thickness of the optical component.

Furthermore, in the case of a Fourier domain type OCT apparatus which uses a plurality of wavelengths, the optical path lengths vary depending on every wavelength according to a scanned position. In the optical component such as the dichroic mirror and the lens, the dispersion characteristics according to the wavelength of the light vary, and the amount of phase shift varies depending on every wavelength. A method for correcting the dispersion characteristics includes a technique exemplified in Japanese Patent Application Laid-Open No. 2011-214968.

When the eye to be inspected is scanned with a light beam with the use of the above described configuration, the intensity and the optical path length of the light beam vary depending on every scanned position on the eye to be inspected, according to the optical component in the optical path. If this difference between the optical path lengths is large, there is a possibility that the focusing positions on the eye to be inspected vary depending on every scanned position, the contrast of the tomographic image becomes low, and layer detecting accuracy is lowered. Specifically, there is a possibility that the contrast of the tomographic image and the like is lowered according to the scanned position with the measuring light on the eye to be inspected.

SUMMARY OF THE INVENTION

The present invention is designed with respect to the above described problems, and an object of the present invention is to provide an optical interference tomographic apparatus which can obtain a tomographic image having a desired contrast and the like, regardless of a scanned position, and to provide a method for controlling the optical interference tomographic apparatus.

In view of the above described problems, the optical interference tomographic apparatus according to the present invention is an optical interference tomographic apparatus which acquires a tomographic image of a predetermined part of an object to be inspected, based on the intensity of interference light obtained by combining return light from the object to be inspected that has been irradiated with measuring light, with reference light corresponding to measuring light, and includes: a scanning optical system which scans the object to be inspected with the measuring light on an optical path of the measuring light; an image forming unit which generates the tomographic image based on the intensity of the interference light; and an image correcting unit which subjects the tomographic image to a correction process appropriate to a scanned position with the measuring light on the object to be inspected.

The optical interference tomographic apparatus according to the present invention can acquire a tomographic image with high precision regardless of the scanned position on the eye to be inspected.

Further features of the present invention will become apparent from the following description of exemplary embodiments with reference to the attached drawings.

BRIEF DESCRIPTION OF THE DRAWINGS

FIG. 3A is a view exemplifying a state in which a fundus of an eye to be inspected is scanned with measuring light.

FIG. 3B is a front view of the eye to be inspected.

FIG. 3C is a front view of the fundus of the eye to be inspected.

FIG. 4 is a view illustrating one example of the obtained tomographic image.

DESCRIPTION OF THE EMBODIMENTS

Preferred embodiments of the present invention will now be described in detail in accordance with the accompanying drawings.

Incidentally, the following embodiments do not limit the present invention involving the scope of the claims, and all of combinations of features described in the present embodiments are not necessarily indispensable for the means for solving the problem in the invention. In addition, the same reference number designates the same component throughout the following description.

Figure 1:
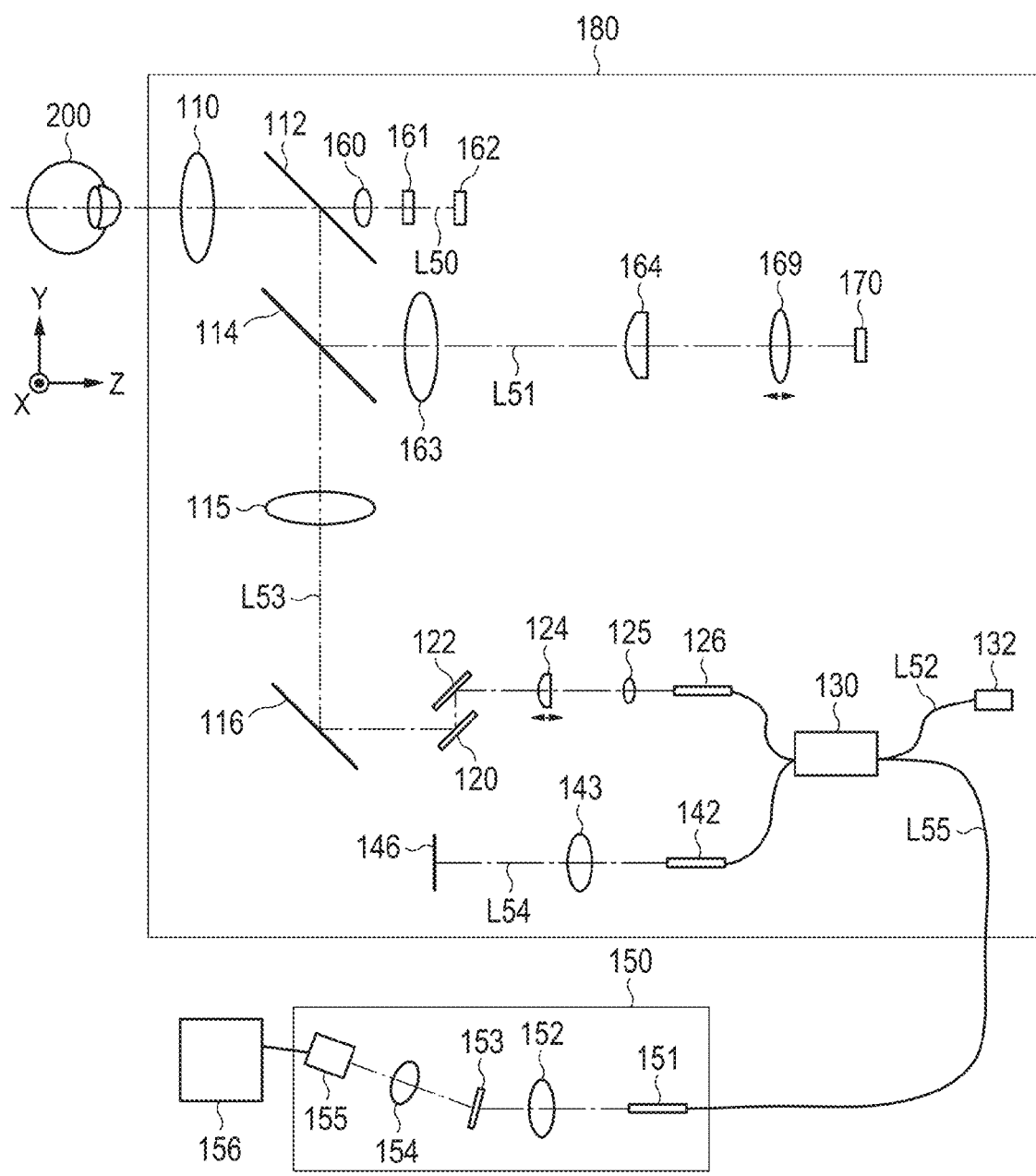
FIG. 1 is a view illustrating a schematic configuration of an OCT apparatus according to a first embodiment of the present invention.

FIG. 1 illustrates a block diagram of an OCT apparatus in the present embodiment. The OCT apparatus has an optical head 180 and a spectroscope 150. The optical head 180 has a mechanism for scanning the eye 200 to be inspected with measuring light, and a mechanism for making return light reflected from the eye 200 to be inspected interfere with reference light. The spectroscope 150 has a mechanism for processing interference light provided by the optical head 180, as a tomographic image. The OCT apparatus which is the optical interference tomographic apparatus acquires a tomographic image of a predetermined part in the eye 200 to be inspected through the spectroscope 150, based on the intensity of interference light, which is obtained by combining the return light reflected from the eye 200 to be inspected that has been irradiated with the measuring light sent from the optical head 180, with the reference light that corresponds to the measuring light and will be described later. In other words, the optical head 180 and the spectroscope 150 cooperate to form an interference optical system for scanning the eye 200 to be inspected with the measuring light, obtaining an intensity distribution of the interference light in a depth direction in the predetermined part the fundus, and acquiring a tomographic image of the predetermined part.

In the optical head 180, optical paths L50 to L55 are arranged, on which each of the optical elements is arranged. On the optical path L50 for observing an anterior ocular, an optical element for observing the anterior ocular of the eye to be inspected is arranged. On the optical path L51 for a fixation lamp, an optical element for making the eye to be inspected fixate on the fixation lamp is arranged. On the optical path L52, optical elements in between a light source and a branch portion of the measuring light and the reference light are arranged. On the optical path L53 for the measuring light, optical elements for irradiating the eye to be inspected with the measuring light are arranged. The optical path L54 for the reference light is an optical path for the reference light for obtaining the interference light. The optical path L55 for the interference light forms an optical path which guides the interference light to the spectroscope 150.

On the optical path L50 for observing the anterior ocular, an anterior ocular observation lens 160, a filter 161 for observing the anterior ocular and a CCD 162 for observing the anterior ocular part of the eye to be inspected are arranged. This CCD 162 for observing the anterior ocular has sensitivity in a wavelength of an unillustrated light source for illumination, specifically, in the vicinity of 970 nm. The illumination, light source irradiates the eye 200 to be inspected with light having a wavelength band different from that of the measuring light which will be described later. The illumination light passes through a first dichroic mirror 112, passes through the lens 110, and reaches the eye to be inspected. The illumination light which has been reflected by the eye to be inspected reversely passes the same optical path, and forms an observation image on the CCD 162. These dichroic mirrors function as optical members which separate the optical paths of the light that reaches the eye 200 to be inspected, and the light, that has been reflected by the eye 200 to be inspected, or divides both of the light into two, according to the wavelength band.

The optical path L51 for making the eye to be inspected fixate on a fixation lamp is provided with lenses 163 and 164 for the fixation lamp, and has a lens 169 for adjusting a focus of the fixation lamp.

The light emitted from the fixation lamp 170 is reflected by a second dichroic mirror 114, is reflected by the first dichroic mirror 112, and reaches the eye 200 to be inspected.

The optical path L52 from the light source is provided with an optical coupler 130 which branches light from the light source into a measuring light path and a reference light path. The optical coupler 130 branches light into the measuring light and the reference light. The branched light beams pass through the dedicated optical paths L53 and L54, respectively, and then are combined by the optical coupler 130 again. The combined light is branched to the optical path L52 for the light source and the optical path L55 for the interference light again. Incidentally, at this time, the combined interference light may pass through the optical path L55. Accordingly, an isolator or the like may be arranged on the optical path L52, or a branching ratio in the optical coupler 130 may be determined so that light in the optical path L52 side becomes smaller. In addition, each of the optical paths reaching the optical coupler 130 shall be connected by an optical fiber.

A light source 132 can employ an SLD which is a representative low-coherence light source. In the present embodiment, a center wavelength of the measuring light which is emitted from the light source 132 is 855 nm, and a wavelength width thereof is approximately 100 nm. The type the light source and the wavelength width can be selected according to the spectroscope 150 which acquires the interference light. In the present embodiment, the above described light source is selected so as to enhance a resolution of the tomographic signal, but other light sources or light having other wavelengths can be also used.

On the optical path L53 for the measuring light, the light emitted from the light source 132 on the optical path L52 is transmitted from a fiber end 126. On the optical path L53, lenses 125, 124, 115 and 110, a mirror 116, an X scanner 120 and a Y scanner 122 are arranged. The lens 124 for adjusting the focus of the measuring light is a lens for adjusting the focus, and is bidirectionally driven on the optical axis L53 by an unillustrated motor. In addition, the X scanner 120 and the Y scanner 122 are operated by driving of unillustrated motors, respectively. The measuring light which has been emitted from the fiber end 126 passes through these optical elements, subsequently further passes through the second dichroic mirror 114, is reflected by the first dichroic mirror 112, and reaches the eye 200 to be inspected.

Figure 2:
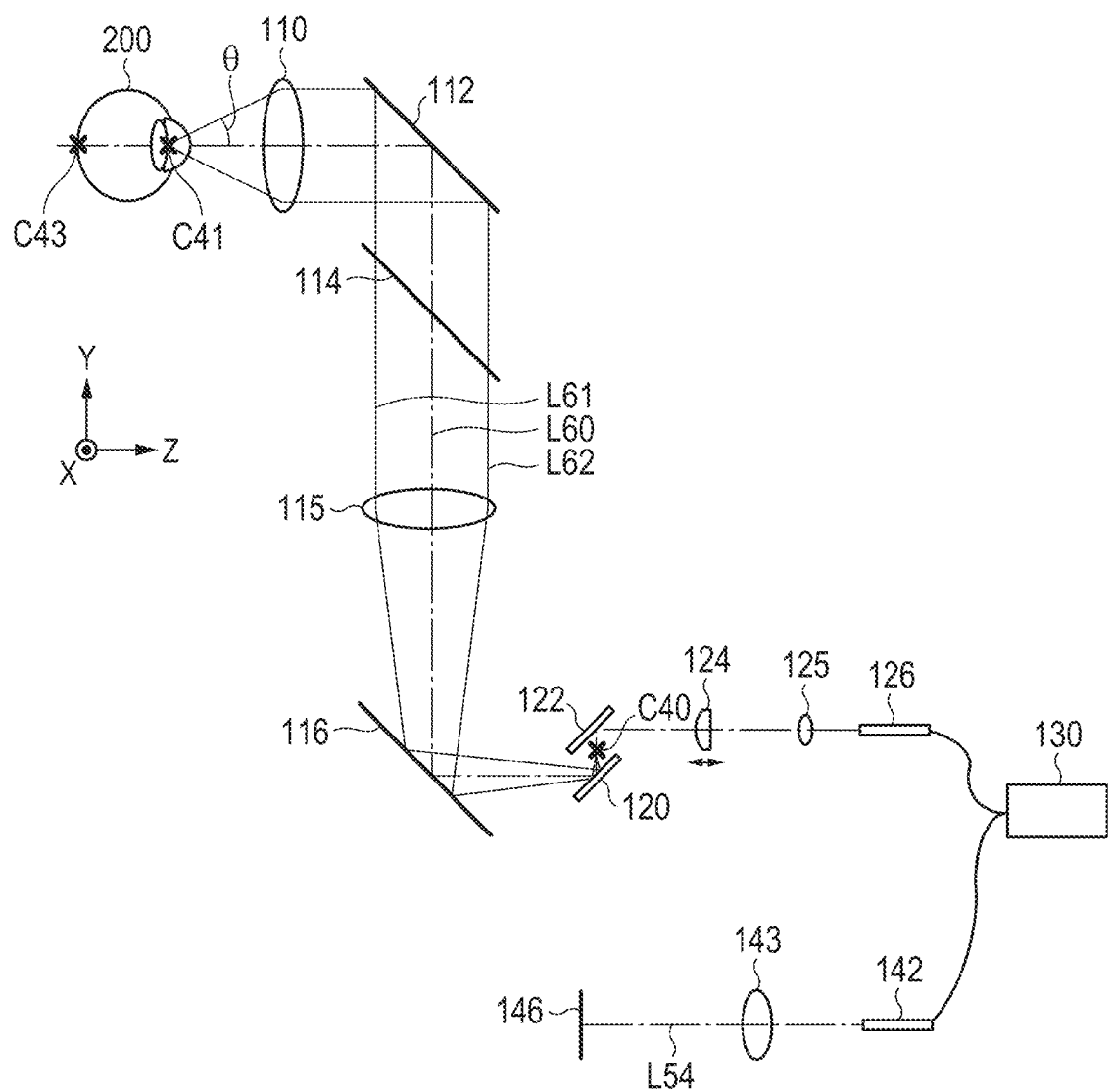
FIG. 2 is a view illustrating a conjugation relationship of optical elements in optical paths of measuring light, in the configuration illustrated in FIG. 1.

The optical elements on the optical path L53 are arranged so that a position conjugate with a predetermined site such as the anterior ocular part of the eye to be inspected exists in between the X scanner 120 and the Y scanner 122, in the present embodiment, the optical elements satisfy the above described configuration, and the incident angle of the measuring light incident on the eye 200 to be inspected is changed by the X scanner 120 and the Y scanner 122. The arrangement of these conjugate positions in the present embodiment is illustrated in FIG. 2. A center position C40 in between the X scanner 120 and the Y scanner 122 has a conjugate relationship with a pupil position C41 in the eye 200 to be inspected. Incidentally, in the present embodiment, these scanners constitute a scanning optical system which scans the eye 200 to be inspected with the measuring light in the optical path of the measuring light. In addition, the X scanner 120 corresponds to a first scanning optical system which scans the eye 200 to be inspected with the measuring light in a first direction, and the Y scanner 122 corresponds to a second scanning optical system which scans the eye 200 to be inspected with the measuring light in a second direction that intersects with the first direction, respectively. Furthermore, as described here, the center position C40 which exists in between these first and second scanners is arranged as a position conjugate with a tomographic image acquiring position which is a predetermined position on the eye 200 to be inspected.

In addition, the fiber end 126 of the measuring light has a conjugate relationship with a fundus portion C43 of the eye to be inspected. The position on the optical axis L53 of the lens 124 for adjusting the focus of the measuring light is adjusted so that the measuring light emitted from the fiber end 126 forms an image on the fundus C43. In the present embodiment, the lens 124 for adjusting the focus is arranged between the fiber end 126 of the measuring light and a set of the X scanner 120 and the Y scanner 122. Thereby, the lens 115 having a comparatively large diameter and the fiber end 126 do not need to be moved in the optical path, and the return light reflected from the eye 200 to be inspected can be efficiently transmitted to the optical coupler 130.

In addition, in the present embodiment, the lens 110 and the lens 115 are arranged so that each of the optical axes approximately perpendicularly intersects with each other. According to this configuration, it is enabled to equalize the incident angle of the measuring light incident on the first dichroic mirror 112 to that incident on the second dichroic mirror 114, when the X scanner 120 and the Y scanner 122 are operated.

As has been described above, the measuring light passes through the second dichroic mirror 114, is reflected by the first dichroic mirror 112, and reaches the eye 200 to be inspected. The measuring light which has been reflected by the eye 200 to be inspected reversely passes through the same optical path, and returns to the fiber end 126 of the optical fiber.

A lens 143 and a reference mirror 146 are arranged on the optical path 154 of the reference light.

The return light which has passed through the optical path L53 and has been reflected from the eye 200 to be inspected is combined with the return light which has passed through the optical path L54 and has been reflected from the reference mirror 146, by the optical coupler 130. At this time, when each of the optical path lengths of the optical path L53 and the optical path L54 become almost the same, interference occurs.

This interference light is passed through a lens 152, becomes approximately parallel light, and is further spectrally dispersed by a diffraction grating 153. The spectrally dispersed light forms an image on a line sensor 155 through a lens 154. Signals obtained in the line sensor 155 are processed by a signal processing section 156, and the tomographic image of the eye to be inspected is obtained based on the signals. The configuration of generating the tomographic image based on the signal processing section 156 and the signal obtained from the signal processing section 156 corresponds to an image forming unit for generating the tomographic image based on the intensity of the interference light in the present embodiment.

FIG. 3A illustrates a state in which a fundus is irradiated with measuring light through a pupil of the eye 200 to be inspected, and the fundus is scanned with the measuring light. FIG. 3A illustrates such a state that the pupil illustrated in FIG. 3B which is a front view 210 of the eye 200 to be inspected is irradiated with the measuring light from a Z direction in FIG. 3A, which is perpendicular to the pupil, and such a state that measuring light 204 is incident on the pupil from a direction which is shifted to a Y direction in FIG. 3A by an angle θ. The incident measuring light 204 is scattered by the retina and the choroid on the fundus (C43 to become conjugate) of the eye 200 to be inspected, and becomes return light which travels in the optical path L53 in a reverse direction to the measuring light. On the fundus, the intensity of the scattered light by a blood vessel or the central fovea varies as is illustrated in a fundus surface view 220 in FIG. 3C.

A luminance distribution in the depth direction on the line sensor 155, which is obtained at an arbitrary position in the Y direction on the fundus of the eye 200 to be inspected, is subjected to an FFT (fast Fourier transform) process in the signal processing section 156. The signal processing section 156 further maps the linear luminance distribution which has been obtained by the FFT process to form an A scan image at the position on the fundus. A plurality of thus obtained A scan images are acquired, for instance, in the Y direction, then these images are continuously arranged, and thereby a tomographic image 230 illustrated in FIG. 4 is structured.

As for scanning, a B scan tomographic image in a desired range of the eye to be inspected may be acquired. In addition, a method for acquiring the B scan image is not limited to a method of scanning the eye with the measuring light linearly in each of the X and Y directions. For instance, it is acceptable to express the desired range of the eye to be inspected, by a distance from the center and a rotation angle, and scan the range in a circular form.

The signal processing section 156 has a previously acquired position correction function recorded therein. A method for acquiring the position correction function will be described below.

The intensity of the interference signal is defined by the following already known expression.

$$I_{int} = I_{ref} + I_{obj} + 2\sqrt{I_{ref}I_{obj}} \cos(kz_{r\_ang} + \phi_{\_ang}(k)) \quad (1)$$

Here, $I_{ref}$ in the expression represents the intensity of the reference light of the optical path L54, and $I_{obj}$ in the expression represents the intensity of the measuring light of the optical path L53. The $I_{ref}$ and $I_{obj}$ are the intensity of the return light which has passed through the optical path L54 and has been reflected by the reference mirror 146, and the intensity of the return light which has passed through the optical path L53 and has been reflected by the eye 200 to be inspected, respectively. The $I_{ref}$ and $I_{obj}$ can be obtained, for instance, by arranging shutters on the reference light path L54 and the measuring light path L53, respectively, blocking one optical path using the shutter, and acquiring the intensity of the light which has passed through the other optical path, by the line sensor 155, similarly to the intensity of the interference light. The expression obtained by having calculated a difference between the intensities of the respective single light beams of the optical paths is defined below.

$$I = \cos(kz_{r\_ang} + \phi_{\_ang}(k)) \quad (2)$$

Here, in the expression, k represents a frequency (k=2π/λ), $z_{r\_ang}$ represents a z coordinate of the eye to be inspected in FIG. 1, and $\phi_{\_ang}$ represents the amount of phase shift in every frequency according to the phase characteristics of the dichroic mirrors which are arranged in the optical paths L53 and L54. Values of $z_{r\_ang}$ and $\phi_{\_ang}$ vary depending on the scanning positions of the X scanner 120 and the Y scanner 122.

As for the phase term of the cosine, which is expressed in the Expression (2) and contributes to the interference, the phase term in arbitrary scanning positions of the X scanner 120 and the Y scanner 122, in other words, in the case where the light with an angle θ of view in FIG. 2 is incident on the eye 200 to be inspected, and the phase term in the case where the angle θ of view is 0 degree, are defined below.

$$A_{\theta=0} = kz_r + \phi(k) \quad (3)$$

$$A_\theta = k(z_r + r_{r\_ang}) + \phi_{\_ang}(k) \quad (4)$$

In the present invention, terms to be corrected are those concerning $\phi(k)$, $z_{r\_ang}$ and $\phi_{\_ang}(k)$. The $z_r$ and $\phi(k)$ are the z coordinate and the amount of the phase shift at the center of the angle of view, and the $z_{r\_ang}$ and $\phi_{\_ang}(k)$ are the Z coordinate and the amount of the phase shift when the angle of view is θ.

Incidentally, when the above described intensity information on the measuring light and the reference light is obtained, the intensity distribution of the reference light can be obtained by using a reference light shutter which is arranged on the optical path of the reference light and temporarily interrupts the reference light, and the light-receiving unit which obtains the intensity of the interference light. In addition, at the same time, the intensity distribution of the measuring light can be obtained by using a measuring light shutter which is arranged on the optical path of the measuring light and interrupts the measuring light, and a light-receiving unit. The plurality of shutters and the line sensor 155 which is the light-receiving unit function as an intensity acquiring unit that is arranged in the present embodiment, including the information processing section 156 which performs signal process.

Here, the method for acquiring the above described correction function will be described below. In order to acquire the correction function, a return mirror is arranged at a position corresponding to the fundus C43 of the eye 200 to be inspected. The phase characteristics of this mirror shall be already known. Incidentally, the return mirror may be arranged at a position corresponding to the anterior ocular part, if the purpose is to measure the anterior ocular part of the eye 200 to be inspected. As for this return mirror, the mirror may be structured so that the inclination can change on every scanned position so that reflected light returns to the optical path L53 again, or a mirror having such a curvature that the reflected light is returned on every scanned position may be arranged. Alternatively, the measuring light may be scanned while the angle of the return mirror is changed along the curvature approximated to the shape of the fundus, so as to return the reflected light to the optical path L53.

Figure 5A:
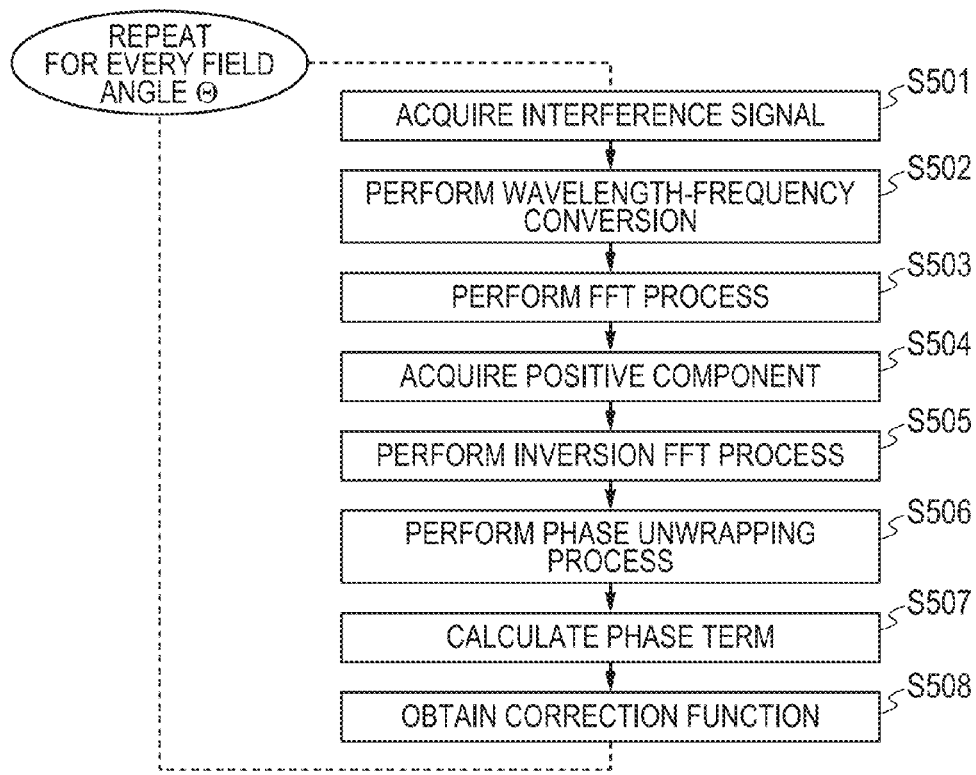
FIG. 5A is a flow chart which illustrates a flow for acquiring a correction function and a procedure of retrieving a phase term in an interference signal.
Figure 5B:
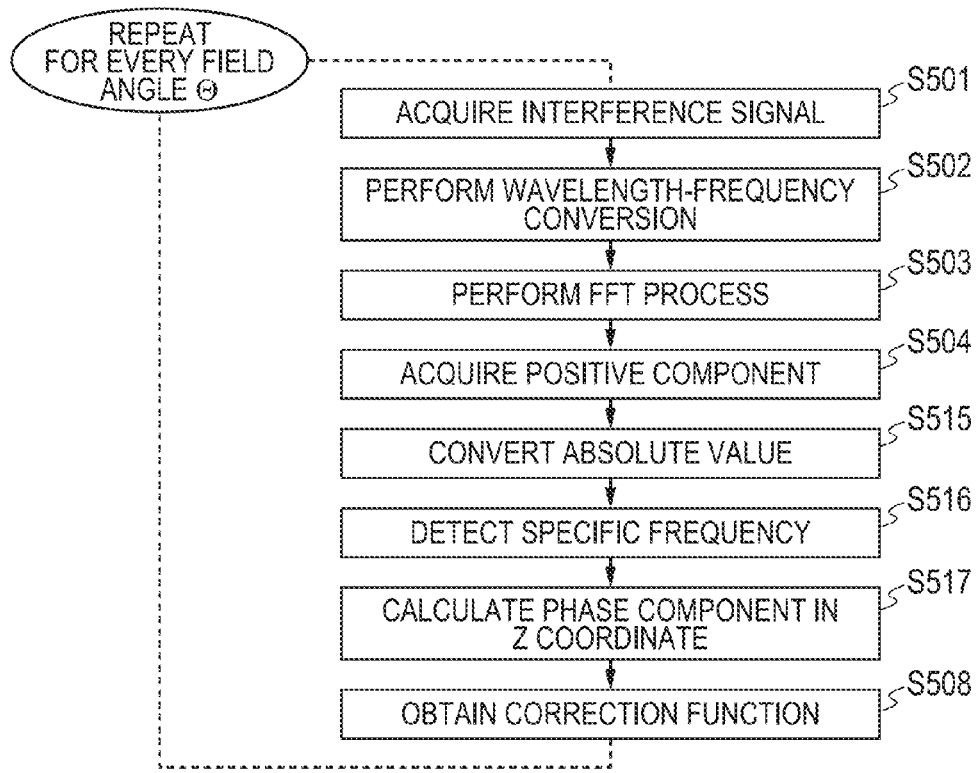
FIG. 5B is a flow chart which illustrates a flow for acquiring a correction function and a procedure of retrieving a phase term in a Z coordinate.

Flows for acquiring the correction function with the use of the above described return mirror are illustrated in FIG. 5A and FIG. 5B.

In FIG. 5A, firstly, in a step S501, an interference signal at the center of the angle of view, at which the angle θ of view is 0, is acquired by the line sensor 155. In a step S502, the information processing section 156 converts the intensity distribution with respect to the wavelength of the interference signal into the intensity distribution with respect to the frequency. The intensity distribution is acquired by using the above described method, the intensity of the reference light and the intensity of the measuring light which have been converted into the intensity distribution with respect to frequency are subjected to differentiation, respectively, and the difference is subjected to the FFT process in a step S503. The difference between the intensity of the reference light and the intensity of the measuring light is calculated in the information processing section 156, by a module region which functions as a difference calculating unit for calculating the difference between the intensity of the reference light and the intensity of the measuring light which have been obtained by the above described intensity acquiring unit.

In a step S504, the signal which has been subjected to the FFT process is passed through an HPF (high-pass filter), and only a positive component obtained in the FFT process is acquired. By the above steps, the positive component of the interference signal at the center of the angle of view is obtained.

The positive component of the interference signal at the center of the angle of view, which has been subjected to the above described process, is processed according to each of two flows which will be described in detail below. Incidentally, steps up to the above described step of acquiring the positive component are the same, and accordingly the following description will be omitted.

The flow illustrated in FIG. 5A illustrates a procedure for retrieving a phase term of an interference signal in Expression (3). The flow illustrated in FIG. 5B illustrates a procedure for calculating a phase term in a Z coordinate in Expression (3).

In the flow of retrieving the phase term of the interference signal, the positive component of the interference signal which has been previously acquired in the step S501 to the step S504 is subjected to an inversion FFT process, in a step S505. Subsequently, an argument component of the obtained interference signal is retrieved; the argument component is subjected to a phase unwrapping process, in a step S506; and the phase term of the interference signal is acquired as a continuous function, in a step S507. Thereby, the phase term of the interference signal in the correction function illustrated in a step S508 is obtained. The above described steps are executed by a module region which functions as a phase term acquiring unit in the information processing section 156.

The interference light which has been acquired in each of the angles θ of view is also similarly subjected to a procedure for acquiring the phase term which is determined in the flow illustrated in FIG. 5A. Thereby, the phase terms of the interference light in each of the angles θ of view are acquired, respectively.

In the flow illustrated in FIG. 5B, in which the phase is restructured, firstly, in a step S515, the positive component of the interference signal which has been previously acquired the step S501 to the step S504 is converted into an absolute value. Subsequently, in a step S516, the peak frequency of the signal is detected which has been obtained from the absolute value. The obtained signal has a function of having a spread in the vicinity of the peak frequency, and accordingly specific frequency and intensity are determined according to a signal process of the apparatus. In a step S517, a phase component y(k) in the z coordinate of Expression (3) is calculated from the specific frequency f which has been obtained in the step S516, by using Expression (5). N is a pixel number of the line sensor 155. Incidentally, the calculation of this phase component is executed by a module region which functions as a phase component calculating unit that acquires the specific frequency of the interference signal and calculates the phase component, in the information processing section 156.

$$y(k) = kz_r = 2\pi f \frac{k}{N} \tag{5}$$

As has been described above, differences between the phase terms of each of the angles θ of view and the phase terms which have been obtained for the phase restructuring are determined, respectively, for each of the phase terms which have been obtained from the two flows. The results become the correction function (S508). The difference process of subtracting the phase components of the specific frequencies from the respective phase terms is executed by a module region which functions as a phase component differentiation unit in the information processing section 156, in the present embodiment. The difference process is shown in Expressions (6) and (7).

$$A'_{\theta=0}(k) = kz_r + \phi(k) - y(k) = \phi(k) \tag{6}$$

$$A'_\theta(k) = k(z_r + z_{r\_ang}) + \phi_{\_ang}(k) - y(k) = kz_{r\_ang} + \phi_{\_ang}(k) \tag{7}$$

In addition, it is also possible to record the intensity of the specific frequency, which is simultaneously obtained, in a form of a ratio with reference to a value obtained when the angle of view is 0, at the same time when the correction function is recorded, and to use the recorded value for correcting an interference waveform intensity when the tomographic image is structured.

The correction function obtained in the above process is stored in the information processing section 156, and is used when the tomographic image of the eye 200 to be inspected is structured. The storage of the phase correction function for correcting the optical path length corresponding to the scanned position is executed by a module region which is arranged in the information processing section 156 and the like, and functions as a storage unit.

Here, when the tomographic image is obtained by irradiation with the measuring light, the optical path length of the measuring light to the fundus varies depending on the incident angle of the measuring light due to the shape of the fundus, as has been described above, and the phase difference between the measuring light path and the reference light path results in being produced. This phase difference results in overlapping the phase difference on the optical path length, which is produced on interfaces of various layers in the fundus of the eye to be inspected, which is desired to be originally acquired, and this phase difference cannot be simply distinguished from the interference signal. However, information from the various layers under the fundus except for the phase difference depending on the incident angle can be obtained by using the above described correction function.

The intensity information of the interference light, can be processed by the phase difference on the various interfaces under the fundus, by subtracting the presented amount of the phase shift based on the obtained correction function. Accordingly, the tomographic image can be obtained which is based on the intensity information in the depth direction at the predetermined position that is irradiated with the measuring light, or at the scanned position. Incidentally, a step of subjecting the tomographic image to a correction process appropriate to the scanned position with the measuring light, on the eye 200 to be inspected to newly structure a tomographic image is executed by a module region which functions as an image correcting unit that is arranged in the information processing section 156 or the like. Specifically, the image correcting unit executes the correction process appropriate to the scanned position with the measuring light, on an object to be inspected, in other words, on the eye to be inspected, with respect to the tomographic image. This image correction unit subjects the intensity of the interference light to the correction process by using the phase correction function stored in the above described storage unit, and restructures the tomographic image. Alternatively, the module region functions also as a unit for correcting the intensity of the signal which is obtained from the interference light, in response to the position on the fundus which is scanned, when the fundus is scanned with the measuring light.

In addition, as for a method of applying the correction to this tomographic image, methods which will be described below can also be employed.

Specifically, such a method may also be employed as to acquire the phase term of the interference light of the eye 200 to be inspected, by using the method of calculating the phase term of the interference light in FIG. 5A concerning a flow for acquiring the correction function, and determine a difference between the acquired phase term and the correction function to restructure the interference signal.

In addition, a method for multiplying the interference light, by the correction function may also be employed. The wavelength of the interference right of the eye 200 to be inspected, which has been acquired in the line sensor 155, is converted into the frequency; the result is converted into a complex number; and the obtained complex function is multiplied by the correction function. Out of the results of this calculation process, the components of the interference light, which are shown in Expression (2), are expressed by Expressions (8) and (9).

$$I_{\theta=0} \exp\{i(kz_r + \phi(k) - i(kz_r + \phi(k))\} \exp\{-iA'_{\theta=0}(k)\} \tag{8}$$

$$I_\theta = \exp\{i[(k(z_r + z_{r\_ang}) + \phi_{\_ang}(k)] - i[(k(z_r + z_{r\_ang}) + \phi_{\_ang}(k)]\} \exp\{-iA'_\theta(k)\} \tag{9}$$

The second terms of the multiplications expressed in the above described Expressions (8) and (9) show a function for correcting a normal image when the interference light is subjected to the FFT process. By inverting and multiplying the symbol of the correction function, a negative image can be corrected.

The above described operations are performed on the A scan tomographic signals which are obtained by the scanning of the eye 200 to be inspected with the X and Y scanners, respectively. Thereby, even in the case where a difference between the optical path lengths occurs due to scanning on the fundus of the eye to be inspected with the measuring light, for instance, the A scanning tomographic image having a desired contrast and the like is obtained regardless of the scanned position. In addition, when the A scanning images which have been obtained by the correction are combined, a suitable B scanning tomographic image is obtained without being influenced by the shape of the fundus of the eye to be inspected and the like.

Other Exemplary Embodiments

In addition, the present invention is achieved also by executing the above described processes or controlling methods. Specifically, such a process also constitutes one embodiment of the present invention as to supply a software (program) which achieves the function of the above described embodiment to a system or an apparatus through a network or various storage media, and make the system or a computer of the apparatus (or CPU, MPU or the like) read out and execute the program.

Furthermore, the present invention is not limited to the above described exemplary embodiments, but can be modified and changed in various ways in such a range as not to deviate from the scope of the present invention, when being carried out. For instance, in the above described embodiment, the case is described where an object to be measured is the eye, in particular, a fundus, but the present invention can also be applied to an object to be measured such as a skin and an organ other than the eye. In this case, the present invention has an aspect, for instance, as medical equipment such as an endoscope other than an optical interference tomographic apparatus working as an ophthalmologic apparatus. Accordingly, it is desirable that the present invention is grasped as one aspect of an inspection apparatus exemplified by the ophthalmologic apparatus, and the eye to be inspected is grasped as one aspect of the object to be inspected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-112609, filed May 30, 2014, which is hereby incorporated by reference herein in its entirety.

What is claimed is:

1. An optical interference tomographic apparatus which acquires a tomographic image of a predetermined part of an object to be inspected, based on intensity of interference light obtained by combining return light from the object to be inspected that has been irradiated with measuring light, with reference light corresponding to the measuring light, the optical interference tomographic apparatus comprising:
a scanning optical system which scans the object to be inspected with the measuring light in an optical path of the measuring light;
an image forming unit which generates the tomographic image based on the intensity of the interference light; and
an image correcting unit which corrects a phase of the interference light on a scanned position on the object to be inspected so as to correct a phase shift generated by difference of incident angles of the measuring light onto an object to be inspected.

2. The optical interference tomographic apparatus according to claim 1, wherein the scanning optical system comprises a first scanning optical system which scans the object to be inspected with the measuring light in a first direction, and a second scanning optical system which scans the object to be inspected with the measuring light in a second direction that intersects with the first scanning direction, and wherein a position conjugate with the predetermined part of the object to be inspected is arranged so as to be set in between the first and second scanning optical systems.

3. The optical interference tomographic apparatus according to claim 1, further comprising:
a storage unit which stores a phase correction function that corrects the phase shift caused by a difference of optical path lengths of the measuring light according to the scanned position with the measuring light on the object to be inspected, wherein the image correcting unit performs a correction process by using the phase correction function.

4. The optical interference tomographic apparatus according to claim 1, further comprising:
an intensity acquiring unit for acquiring a phase term of each of light intensities of the measuring light which is reflected by a mirror instead of the object to be inspected, and the reference light;
a phase term acquiring unit for acquiring the phase term appropriate to the scanned position with the measuring light on the object to be inspected, from an interference signal based on the interference light obtained by combining the reference light and the measuring light reflected by the mirror; and
a phase component calculating unit for calculating a difference between the phase term of the measuring light and the phase term of the reference light obtained by the phase term acquiring unit based on an intensity distribution of the interference light, which is acquired by the intensity acquiring unit,
wherein the image correcting unit corrects the phase of the interference light obtained from the object to be inspected by using the difference.

5. The optical interference tomographic apparatus according to claim 4, wherein the intensity acquiring unit (1) obtains the intensity distribution of the reference light by using (a) a reference light shutter that is arranged on the optical path of the reference light and interrupts the reference light, and (b) a light-receiving unit which obtains the intensity of the interference light, and (2) obtains the intensity distribution of the measuring light by using a measuring light shutter that is arranged on the optical path of the measuring light and interrupts the measuring light, and the light-receiving unit, and
wherein the difference calculating unit calculates a difference between the intensity of the reference light and the intensity of the measuring light that have been obtained by the intensity acquiring unit.

6. The optical interference tomographic apparatus according to claim 1, further comprising:
a mechanism for driving a lens for adjusting a focus of the measuring light, on the optical path of the measuring light;
a mechanism for changing an optical path length of the reference light;
a mechanism for irradiating the object to be inspected with light having a wavelength band different from that of the measuring light; and
an optical member which divides the optical path according to the wavelength band.

7. An optical interference tomographic apparatus which acquires a tomographic image of a predetermined part of an object to be inspected, based on intensity of interference light obtained by combining return light from the object to be inspected that has been irradiated with measuring light, with reference light corresponding to the measuring light, the optical interference tomographic apparatus comprising:
an interference optical system which scans the object to be inspected with the measuring light, obtains the intensity distribution of the interference light in a depth direction at the predetermined part of the object to be inspected, and acquires a tomographic image of the predetermined part of the object to be inspected; and
a unit for correcting the intensity of signal which is obtained from the interference light, according to a scanned position of the measuring light on the object to be inspected when the scan is performed, to correct a phase shift generated by difference of incident angles of the measuring light onto an object to be inspected.

8. A storage medium having a program which makes a computer function as each unit of the optical interference tomographic apparatus according to claim 1.

9. A method for controlling an optical interference tomographic apparatus which acquires a tomographic image of a predetermined part of an object to be inspected, based on intensity of interference light obtained by combining return light from the object to be inspected that has been irradiated with measuring light, with reference light corresponding to the measuring light, the method comprising:
- a step of scanning the object to be inspected with the measuring light, on an optical path of the measuring light;
- an image generating step of generating the tomographic image based on the intensity of the interference light; and
- an image correcting step of subjecting the tomographic image to a correction process appropriate to a scanned position with the measuring light on the object to be inspected, to correct an intensity of signal which is obtained from the interference light, according to the scanned position when the scan is performed, so as to correct a phase shift generated by difference of incident angles of the measuring light onto an object to be inspected.

10. A storage medium having a program which makes a computer execute each step in the method for controlling an optical interference tomographic apparatus according to claim 9.

11. An optical interference tomographic apparatus according to claim 1, wherein the object to be inspected is an eye, and wherein the predetermined part is a fundus of the eye.

12. An optical interference tomographic apparatus according to claim 7, wherein the object to be inspected is an eye, and wherein the predetermined part is a fundus of the eye.

13. An optical interference tomographic apparatus according to claim 1, wherein the phase shift is a shift amount of the phase of the measuring light at a time when the incident angle of the measuring light is $\theta$, for the phase of the measuring light at a time when the incident angle of the measuring light is 0.

14. An optical interference tomographic apparatus according to claim 3, wherein the phase correction function is a function of which parameters are an incident angle of the measuring light and a position in a depth direction of the object to be inspected.

* * * * *